United States Patent [19]

Roach

[11] 4,352,564

[45] Oct. 5, 1982

[54] MISSING ORDER DEFECT DETECTION APPARATUS

[75] Inventor: William R. Roach, Rocky Hill, N.J.

[73] Assignee: RCA Corporation, New York, N.Y.

[21] Appl. No.: 155,989

[22] Filed: May 30, 1980

[51] Int. Cl.³ .............................................. G01N 21/32
[52] U.S. Cl. .................................... 356/354; 250/550; 250/572; 356/237
[58] Field of Search ................... 356/237, 430, 354; 250/550, 572

[56] References Cited

U.S. PATENT DOCUMENTS

| | | | |
|---|---|---|---|
| 3,842,194 | 10/1974 | Clemens | 178/6.6 A |
| 4,030,835 | 6/1977 | Firester et al. | 356/354 |
| 4,044,379 | 8/1977 | Halter | 358/128 |
| 4,069,484 | 1/1978 | Firester et al. | 356/237 X |
| 4,155,098 | 5/1979 | Roach et al. | 250/550 |
| 4,180,830 | 12/1979 | Roach | 356/237 |
| 4,197,011 | 4/1980 | Hudson . | |

Primary Examiner—Bruce Y. Arnold

Attorney, Agent, or Firm—E. M. Whitacre; J. S. Tripoli; J. E. Roehling

[57] ABSTRACT

A defect detection apparatus is disclosed for optically inspecting a spiral groove of a video disc record by directing a coherent light beam at the grooved surface of the disc. The incident beam illuminates the grooved surface with a light spot that spans a plurality of groove convolutions. The structure of the illuminated region on the grooved surface serves as a diffraction grating for diffracting the incident beam into discrete diffraction orders. Relative motion is established between the disc surface and the incident beam in a manner causing the illuminating spot to rapidly scan the grooved surface in a coarse spiral pattern. A lens system is positioned to collect the light from a single beam of a particular group of non-zero diffraction order beams and to focus this non-zero order beam onto a photodetector. When a defect in the groove pattern exists in the illuminated region the measured power of the non-zero order beam will fall below its normal level. The fractional decrease in the measured power is an indication of the relative size of the defect.

8 Claims, 4 Drawing Figures

MISSING ORDER DEFECT DETECTION APPARATUS

The present invention relates generally to optical apparatus for scanning the tracked surface of a record for flaws and, more particularly, to defect detection apparatus employing optical techniques to determine flaws in a surface having track convolutions of uniform spacing of a high density information record, such as a video disc of the type described in U.S. Pat. No. 3,842,194, issued to J. K. Clemens.

The defect detection principles of the present invention are applicable to optical inspection of closely and uniformly spaced track convolutions and spiral grooves for video disc records at various stages throughout the record mastering and replicating processes.

In certain high density information record/playback systems, video information is recorded as relatively short wavelength (e.g., 0.6–1.6 μm) reflectivity, transmission or relief variations along the length of an information track. Illustratively, the method of recording may be of a type shown in U.S. Pat. No. 4,044,379, issued to J. B. Halter. Pursuant to the Halter method, an electromechanically driven stylus (e.g., of diamond), responsive to a video and audio signal, records the relatively short geometric variations representative of the time variations of the signal to be recorded in a metal master. After the electromechanical recording operation, the metal master has a relief pattern corresponding to that which is desired in the final record. Molds for making stampers which are used to produce production line records are made from the master and a vinyl substrate is formed, having the desired relief pattern, from a stamper made from such a mold.

During each of the above-identified record manufacturing processes, various kinds of flaws can develop which may affect the record groove quality and which are difficult to detect in view of the fineness of the groove structure typically employed in a video disc (e.g., 10,000 groove convolutions per inch).

In U.S. Pat. No. 4,030,835, issued to A. H. Firester et al., entitled DEFECT DETECTION SYSTEM, a system for detecting groove structure defects is disclosed that rapidly probes the grooved surface of the methl master, mold or stamper with a light beam in a spiral probing pattern, developing an electrical impulse indication of the illumination of each surface region containing a groove structure defect. The Firester defect detection system illuminates the grooved surface of the part being inspected with a laser beam to thereby produce a diffraction pattern. The pattern from an ideal defect-free disc when projected onto a viewing screen consists of a discrete set of groove diffraction spots along with signal diffraction bands. When a defect is present, light is scattered into regions removed from this ideal pattern. In the Firester system, a detector is arranged to detect very small angle scattering from the zero-order groove diffraction beam. A large area detector is centered directly in front of the zero-order beam, and a small diameter stop is positioned in the center of this detector to interrupt the zero-order beam. With this set-up, a signal impulse from the detector is indicative of the illumination of a defect, i.e., the scattering of the zero-order beam away from the stop.

The Firester system provides satisfactory results when inspecting flat or shallow grooved parts (e.g., parts produced from electroplating resist coated electron-beam recorded substrates), however, the system does not perform quite as well when used for inspecting substrates having certain groove profiles and signal element depths (e.g., disc substrates having a 140° V-shaped groove and 700 Å deep signal elements). It has been found that in such cases the Firester system has difficulty in sensing small defects without being simultaneously sensitive to the relatively deep signal elements. The Firester system assumes that any scattering of the zero-order beam is caused by a defect. Since deep signal elements may also diffract light out of the zero-order beam, the sensitivity of the system cannot be arbitrarily increased by increasing the gain of the photodetector without simultaneously increasing the sensitivity of the system to the presence of signal elements.

In accordance with the principles of the present invention, a system for detecting defects is provided that is not subject to the aforementioned limitations. In this system, the decrease or absence of detected light power in a particular track diffraction order is indicative of a defect. Generally, track diffraction orders correspond to those orders of the diffraction pattern which are generated by the presence of tracks or grooves.

In further accordance with the principles of the present invention, a linearly polarized laser is used in the defect detector. By properly aligning the polarization of the laser on the surface of the sample under inspection, substantially all effects of signal elements can be eliminated so that defects in the track pattern under inspection may be detected with even greater sensitivity and reliability.

In accordance with one aspect of the present invention a flaw detection apparatus for detecting defects in a record surface having uniformly spaced tracks or a spiral groove is provided. The apparatus comprises means for providing a beam of light directed toward a region of the surface of the record along an incident beam path and means for forming the beam of light to an illuminated region being sufficiently large to span a plurality of tracks or groove convolutions. The structure of the tracks or groove convolutions in the surface region illuminated by the light beam, absent any surface defect, serves as a diffraction grating for diffracting the light reflected from the illuminated region to form a zero diffraction order beam of light and higher diffraction order beams of light. Means are provided for establishing relative motion between the surface and the beam path so that successive regions of the surface are scanned by the light beam. A light detection means having a photosensitive surface is positioned at a first location to intercept one of the higher order diffraction beams. A means responsive to signals developed by the light detection means, for indicating illumination of a defect, is also included in the flaw detection apparatus.

Figure 1:
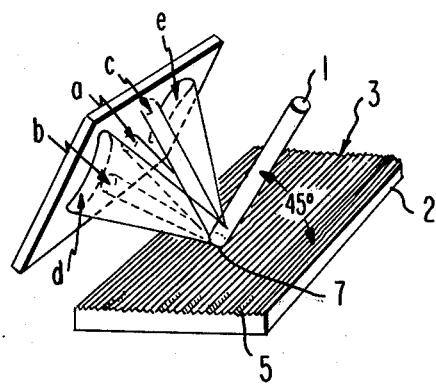
FIG. 1 illustrates an optical schematic of a portion of a diffraction spectrum produced by illuminating a plurality of uniformly spaced grooves having signals recorded therein on a surface such as a video disc surface with a coherent light beam.

Referring to FIG. 1, a laser beam 1 is incident on surface 3 of disc 2 at an angle of approximately 45° with respect to a normal to the disc and lies in a plane which contains a radial of and is perpendicular to the disc surface. A spiral groove 5 (e.g., 140° "V" shaped groove of 0.5 μm depth, of a substantially constant pitch, for example, 10,000 grooves/inch) forms the diffraction grating located on disc surface 3. The signal elements which are recorded across the groove 5 as relatively short geometric variations (e.g., 0.6-1.6 μm) along the length of groove 5 to a depth on the order of 850 Å affects the light reflected from disc surface 3 and may interfere with the proper functioning of a defect detection system.

Light beam 1 which is incident on disc surface 3 is focused such that in the focal region 7 the spot size is much larger than the groove width, thus several convolutions of groove 5 are illuminated simultaneously. The groove and signal element structure in the illuminated region, in the absence of any defects, forms a pattern of depressions and elevations, which effectively serves as a two-dimensional diffraction grating to diffract the light reflected off of disc surface 3 into a well-defined diffraction pattern above the surface 3. The grooves on the surface diffract the light into discrete beams. The lowest three diffraction orders formed as a result of the grooves are shown in FIG. 1 as a, which is the zero groove order, b, which is the "−1" groove order, and c, which is the "+1" groove order. The zero-order coincides with the direction of specular reflection. The signal elements, on the other hand, produce two continuous diffraction fans, d and e, which are displaced symmetrically on each side of the groove order diffraction beams.

Figure 2:
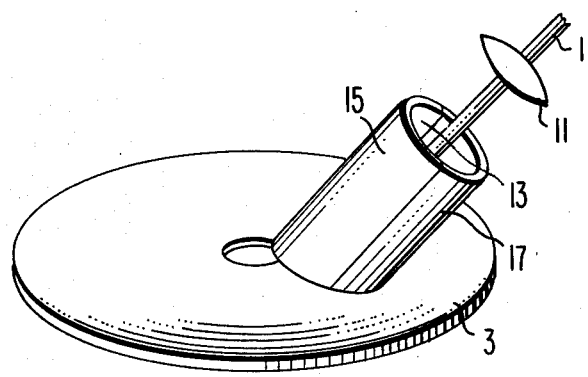
FIG. 2 shows a regularly grooved disc surface irradiated by a coherent light beam where the coherent light beam is enclosed within a cylindrical surface in order to illustrate an underlying principle of the invention.
Figure 3:
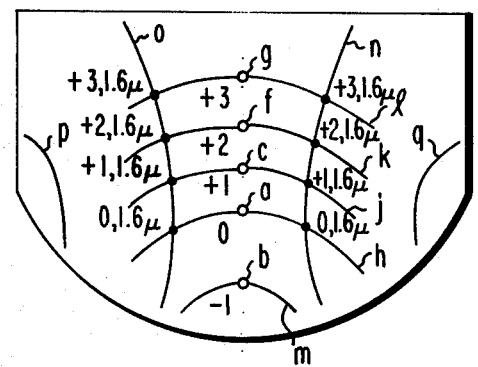
FIG. 3 shows a composite projection of the diffraction pattern produced by illuminating the surface of a disc which is provided with grooves of uniform spacing having signal elements recorded therein onto the inside surface of the cylindrical surface of FIG. 2.

FIGS. 2 and 3 are used to illustrate some of the underlying principles of the present invention. Referring to FIG. 2, a laser beam 1 is focused onto disc surface 3 by lens 11. A spiral groove is provided on disc surface 3 having signal elements recorded across the groove width. A cylindrical semi-transparent viewing screen 13, having a cylindrical axis coincident with the axis of the laser beam 1, is used to enclose the light beam 1 to display the positions of the diffraction pattern. The diffraction pattern which is formed above reflective disc surface 3 projects onto the inside surface of cylinder 13 which is split into two sections 15 and 17.

The projection of the diffraction pattern onto the inside of section 15 of FIG. 2 is illustrated in FIG. 3 which shows section 15 unrolled flat. Diffraction by a grooved surface without signal elements results in a series of spots a, b, c, f and g for the 0, −1, +1, +2 and +3 groove orders respectively. Diffraction by a radial scratch on a flat, ungrooved surface results in a smearing effect as illustrated by line h. Diffraction by a radial scratch on a grooved surface, without signal elements, results in smearing of groove spots as illustrated by lines h, j, k, l and m for the 0, +1, +2, +3 and −1 groove orders respectively. Simultaneous diffraction by groove convolutions and signal elements of a particular wavelength (e.g., 1.6 μm) which are coherently phased from groove convolution to groove convolution would produce a series of spots at the intersections of groove smears h, j, k and l and the lines n and o (e.g., the intersection j, n of this convention corresponds to a simultaneous +1 order diffraction by grooves having a density of approximately 10,000 grooves/inch and +1 order diffraction by a signal grating of 1.6 μm wavelength). Since the signals are actually randomly phased from groove convolution to groove convolution the signal diffraction pattern for a given fixed signal wavelength becomes a pair of bands, for example, n and o or p and q.

FIG. 3 is illustrative in that it shows that simultaneous signal and groove diffraction occurs for the 0, +1, +2 and +3 groove diffraction orders, but, for the "−1" groove diffraction order there is no simultaneous groove and signal diffraction from signal elements shorter than approximately 1.6 μm. Thus, the −1 groove diffraction order may be special in that its intensity is not generally modulated by signal diffraction so that the −1 order power may be affected very little, if at all, by most signal elements recorded on a video disc of a type described in the Clemens patent. Thus, if it is desired to inspect for defects in a deep groove pattern, then the −1 order is a useful order to look at to reduce the influence of signal elements in the groove.

It has been found experimentally, however, that the −1 groove order is somewhat affected by the presence of signal elements if the polarization of the incident light beam is not properly oriented at the disc surface. Referring again to FIG. 1, a linearly polarized light beam 1 having the E-vector tangent to groove 5 affects the −1 diffraction order beam b (i.e., signal elements present in the groove on the disc surface are detected with maximum sensitivity and, therefore, the ability of the system to detect groove defects is decreased). On the other hand, if the linearly polarized source is oriented so that the light beam E-vector is perpendicular to groove 5 the signal elements are almost "invisible" (i.e., signal elements present in the groove on the disc surface are practically undetectable and, therefore, the ability of the system to "see" defects in the groove structure is correspondingly increased).

One way of viewing this polarization orientation phenomenon is as follows. The reflectivity of the surface of the disc depends on the electric field of the light being able to cause unimpeded electron flow along the surface. Steps in the surface (i.e., signal elements) perpendicular to the flow of current effectively increases the path length an electron must travel and, thus, increases the effective resistance of the surface. A high spacial frequency increases the effective surface resistance more than a low spacial frequency. By properly aligning the polarization direction of the laser light beam on the disc surface (i.e., orienting the light beam so that the E-vector is perpendicular to the grooves, or in the radial plane of the disc) the defect detector is very sensitive to the presence of the groove structure but almost totally insensitive to the presence of signal elements of varying spacial frequencies recorded in the groove.

Figure 4:
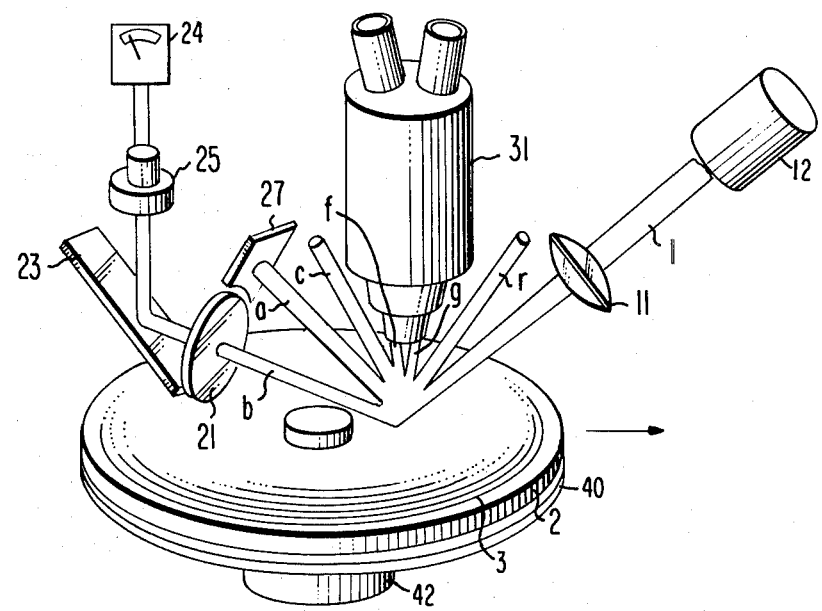
FIG. 4 illustrates a defect detection apparatus constructed in accordance with the principles of the present invention.

A laser defect detector utilizing the principles of the present invention is illustrated in FIG. 4. Laser beam 1 which is emitted by a source of radiation 2, e.g., a laser is focused onto disc surface 3 by lens 11. Laser beam 1 is preferably linearly polarized and oriented so that the E-vector is perpendicular to the groove wall, or, in other words, lies in a radial plane. A spiral groove to be inspected resides on disc surface 3 having signal elements recorded therein. The structure of the grooves and signal elements in the illuminated region of the disc surface 3 serves as a diffraction grating to diffract the light reflected off of disc surface 3 into discrete orders.

The grooves diffract the light beam into discrete beams a (the zero groove order), b (the "−1" groove order), c (the "+1" groove order), f (the "+2" groove order), g (the "+3" groove order) and r (the "+4" groove order). A large aperture lens 21 which lies very close to the disc surface focuses the "−1" groove order beam via mirror 23 onto photodiode detector 25. A baffle 27 is positioned near lens 21 to exclude collection of any portion of the zero-order beam. Again, the −1 groove order beam is specifically detected because of its relative insensitivity to the existence of signal elements in the groove.

A succession of regions of grooved surface 3 are scanned by incident beam 1 in a spiral pattern when relative motion between surface 3 and beam 1 is established by rotating disc 2 on turntable 40 driven by a turntable motor 42 at a first selected rate while translating disc 2 in a radial direction as shown by the arrow (e.g., the turntable drive motor may be mounted on a slide which translates in a radial direction). By selectively choosing these two rates a desired coarseness of the spiral scanning pattern may be accomplished. Various degrees of overlap of the scanning pattern convolutions may be achieved. Desirably the two rates are chosen so that the spiral light scanning pattern has a pitch comparable with the focused spot size but appreciably greater than the disc's grooved pitch so that the entire grooved surface may be scanned for defects in a time span appreciably shorter than the normal playing time for the disc.

The defect indicating output signals of the above-described defect detection system may be used in a variety of ways, e.g., as input to a meter, a counter, a recorder, etc. A particularly advantageous use of such defect indicating signals is to input them to a defect plotting system of the type disclosed in U.S. Pat. No. 4,069,484 issued to Firester et al. on Jan. 17, 1978 entitled, DEFECT PLOTTING SYSTEM.

In the present invention the defect is detected by sensing a missing groove order. Since each non-zero groove order diffraction beam should be present only when grooves are illuminated by the light beam 1, any decrease in the measured power, as measured by meter 24, in one of these orders (e.g., "−1" groove order) should be an indication that the region illuminated by light beam 1 includes a defect. For defects that are small compared to the laser spot diameters the fractional decrease in the output of detector 25 should be a measure of the relative size of the defect. Large groove defects will cause a large decrease in the output signal from detector 25 to occur for a time that is determined by the linear extent of the defect along the groove.

One advantage of the defect detection system described herein compared to the Firester Defect Detection System (U.S. Pat. No. 4,030,835) is its relative insensitivity to surface warp. Since the entire non-zero order beam is collected, this system is not very sensitive to sample surface warp that would simply cause a non-zero order beam to move over the active surface of detector 25.

Referring again to FIG. 4, a high powered microscope 31 is shown mounted above the disc 2. Using the mapping scheme of U.S. Pat. No. 4,069,484, after the disc has been scanned, the leading edge of a mark on the electrosensitive paper can be positioned to bring the corresponding defect into the field of view of the high powered microscope 31. In this manner surface 3 may be inspected while disc 2 is still mounted in the defect detection system.

What is claimed is:

1. A flaw detection apparatus for detecting defects in a record surface having uniformly spaced track convolutions said apparatus comprising:
   first means for providing a beam of light directed toward a region of the surface of said record along an incident beam path;
   second means for focusing said beam of light to illuminate a region of said surface, said illuminated region being sufficiently large to span a plurality of tracks;
   the structure of the track convolutions in the surface region illuminated by said light beam serving as a diffraction grating for diffracting the light from said illuminated region to form a zero diffraction order beam of light and higher diffraction order beams of light, and wherein short wavelength variations in track depth exist along the length of said track convolutions, the structure of said track convolutions and said short wavelength variations serving as a two-dimensional diffraction grating for diffracting the light from the illuminated region into said zero diffraction order beam of light, said higher diffraction order beams of light, and into additional higher diffraction order beams of light which are substantially affected by said short wavelength variations;
   third means for establishing relative motion between said surface and said beam path in such a manner that a succession of regions of said surface are scanned by said light beam;
   fourth means for directing one of said higher diffraction order beams, to the exclusion of said additional higher diffraction order beams, to a first location;
   light detection means having a photosensitive surface positioned to intercept said one higher diffraction order beam at said first location and to provide a detection signal in response to said one higher order diffraction beam; and
   fifth means, responsive to said detection signal developed by said light detection means, for indicating illumination of a defect in said surface.

2. The apparatus according to claim 1 wherein said beam of light from said first means is polarized and wherein said first means is arranged such that the E polarization vector of said light beam is incident on said surface substantially perpendicular to the direction tangent to said tracks.

3. The apparatus according to claim 2 wherein said means for providing said light beam comprises a linearly polarized laser.

4. The apparatus according to claim 1 wherein the orientation of the axis of said incident path relative to a normal to said surface is such that said axis lies in a non-parallel relationship, and at a chosen angle, with respect to said normal to said surface in a plane which contains the central axis of said record.

5. The apparatus according to claim 4 wherein said chosen angle is substantially 45°.

6. The apparatus according to claim 5 wherein said record is in the shape of a disc and wherein said higher diffraction order beams of light include:
   first order diffraction beams diffracted in said plane which intersects said surface along a radius, one of said first order beams being diffracted at an angle as measured in said plane between the axis of said diffracted beam and the surface of said disc which is smaller than the angle which the other of said first order beams makes with said surface as measured in said plane between the axis of the diffracted beam and said surface, said one of said first order beams corresponding to said one of said higher diffraction order beams.

7. The apparatus according to claim 1 further comprising:
    means, in proximity to said fourth means, for preventing reflected light from said surface other than from said one higher diffraction order beam from striking said photosensitive surface.

8. The apparatus according to claim 1 wherein said fifth means for indicating a defect is responsive to the relative size of a defect in said surface.

* * * * *